US00PP12184P2

(12) United States Plant Patent
Littlejohn et al.

(10) Patent No.: US PP12,184 P2
(45) Date of Patent: Nov. 6, 2001

(54) *ORNITHOGALUM DUBIUM* PLANT NAMED 'NAMIB SUN'

(76) Inventors: Gail Littlejohn, Private Bag X1, Elsenberg 7607; E. L. Farringer; C. F. Farringer, both of P.O. Box 145, Groot Drakenstein, 7680, all of (ZA)

( * ) Notice: Subject to any disclaimer, the term of this patent is extended or adjusted under 35 U.S.C. 154(b) by 0 days.

(21) Appl. No.: 09/337,803

(22) Filed: Jun. 21, 1999

(30) Foreign Application Priority Data

Apr. 19, 2000 (ZA) ..... 2002344

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2000/04, GTI JOUVE Retrieval Software, citation for 'NAMIB SUN', Aug. 2000.*

* cited by examiner

*Primary Examiner*—Bruce R. Campell
*Assistant Examiner*—Wendy Baker
(74) *Attorney, Agent, or Firm*—Paul S. Rooy

(57) ABSTRACT

'Namib Sun', an *Ornithogalum dubium* cultivar. 'Namib Sun' has a robust and vigorous growth pattern producing leaves 20–30 cm in length. The most striking characteristic of the mature plant is its spike-shaped inflorescence (raceme) which is between 30 and 50 cm tall and includes 50–60 flowers. The flowers are RHS7B yellow with green centers. Each 'Namib Sun' flower is cup-shaped to stellate with age, and two to three cm wide.

3 Drawing Sheets

FOREIGN PRIORITY

This application claims benefit and priority of Certificate of Grant of a Plant Breeder's Right for Namib Sun, issued Apr. 3, 2000 (South Africa), application for which was filed Oct. 22, 1998.

FIELD OF THE INVENTION

The present invention comprises a new and distinct cultivar of *Ornithogalum dubium* which is named 'Namib Sun'. Its market class is that of potted plants or bulbs. 'Namib Sun' is intended for use in landscaping, and as a decorative flowering potted plant.

DESCRIPTION OF PRIOR ART

'Namib Sun' was invented by hand pollination between two subspecies of *Ornithogalum dubium*. The cross pollination was conducted during 1994 at Elsenberg, Western Cape, Republic of South Africa. 'Namib Sun' was bred and evaluated by Dr. Gail Littlejohn, a citizen of South Africa. 'Namib Sun' was first asexually propagated by Dr. Farringer and Mrs. Farringer. Dr. E. L. Farringer is a U.S. citizen, and Mrs. C. F. Farringer a citizen of the Republic of South Africa.

'Namib Sun' is a cross of A2 (unpatented) and 91H969-3 (unpatented) Ornithogalum. A2 was an *Ornithogalum dubium* selection which was chosen for its large petal size, its yellow flowers, and its long flower raceme. 91H969-3 was an *Ornithogalum dubium* selection which was chosen for its deep yellow flower color.

'Namib Sun' has been asexually reproduced in South Africa from 1997 onwards, using tissue culture. Approximately 20,000 plants have been grown, and these 'Namib Sun' propagules appear to be identical to the original plant in all distinguishing characteristics. Thus the clone appears stable.

SUMMARY OF THE INVENTION

'Namib Sun' is a bulbous plant with strap-like leaves. In nature, it grows in winter and flowers in the spring (October in the Southern hemisphere at 32 degrees South). It produces a long spike-shaped flower raceme of about 20 to 75 cm in height.

'Namib Sun' is cyclically dormant. Specifically, it is dormant in summer, and blooms every year. Plants in nature rarely live beyond 5–10 years due to pests. In a pest-free environment, plants will live in excess of 10 years.

'Namib Sun' is distinguishable from other clones by the color of its flower, the size of flower raceme, and the size of individual florets as well as the robust growth pattern of the leaves. In addition, the plant 'Namib Sun' itself is much more robust than most other *Ornithogalum dubium* varieties. 'Namib Sun' is adapted to Zone 8 of the Hardiness Map of the United States.

'Namib Sun' is distinguished from other *Ornithogalum dubium* cultivars by the following combination of traits:

Flower color: RHS7B yellow.
Flower size: 2–3 cm.
Flower shape: Cup-shaped.
Raceme size: 30–75 cm in height.
Flowers per raceme: 15–20 [50–60].
Leaf size: 20–30 cm.

BRIEF DESCRIPTION OF THE DRAWINGS

The invention, together with the other objects, features, aspects and advantages thereof will be more clearly understood from the following in conjunction with the accompanying drawings.

Three sheets of drawings are provided. Sheet one contains FIG. 1. Sheet two contains FIG. 2. Sheet three contains FIG. 3.

BOTANICAL DESCRIPTION OF THE PLANT

'Namib Sun' is an *Ornithogalum dubium* obtained from the crossing of an *Ornithogalum dubium* subspecies *pillansii* seed parent, designated by the breeder as A2, with an *Ornithogalum dubium*, the pollen parent, selected for its color and designated 91H969-3. The cross was controlled and obtained by emasculation of one parent and hand pollination of pollen from the other. Breeding was undertaken in order to obtain a plant suitable for the ornamental potted plant and bulb market. 'Namib Sun' was asexually reproduced in Groot Drakenstein, South Africa through tissue culture of leaf explants in a solid "Murishage and Skoog" medium. 'Namib Sun' is stable in reproduction because currently 20,000 plants are grown in a soil mixture medium in a tunnel and no instability is observed in the growth of flowering of the propagated material.

At maturity 'Namib Sun' consists of a bulb of 2.5 cm to 8 cm in diameter depending on the number of growth cycles and the horticultural conditions. Generally the bulbs are a slightly flattened ovoid sphere, the horizontal diameter being slightly greater than the vertical diameter when the growing point is situated upwards and the roots downwards.

The plant is normally dormant in the summer (December through March at 32 degrees South in the Southern Hemisphere). When dormant substantially all roots and leaves are dried up and no longer visible. In April–May (all descriptions of plants in nature refer to conditions in the South African Province of the Western Cape which is around 30–32 degrees South latitude) growth resumes from the previous year. The exact timing of growth resumption is dependent on seasonal fluctuations in winter rainfall.

Once growth resumes the leaves, roots and bulb expand and grow. Only once substantial bulb, leaf and root growth occur does flower initiation begin. By the time the flower raceme emerges the leaves are perhaps 90% fully grown. The remaining 10% of growth occurs while the flower raceme expands.

Figure 3:
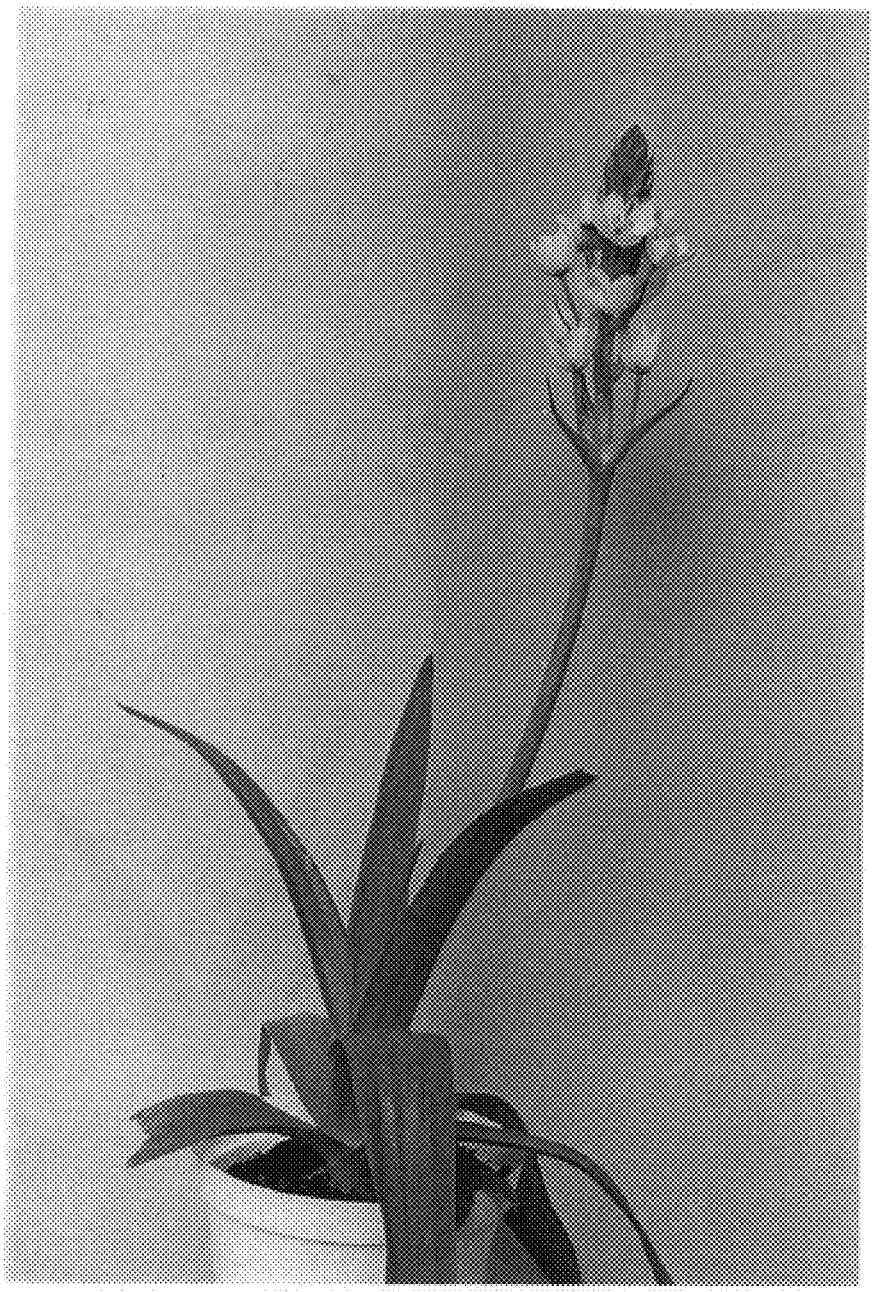
FIG. 3 is a color photograph of a 'Namib Sun' plant showing the plant from its pot to its top, including the leaves.

Leaves are 20 to 30 cm long when mature, and in shape are linear and strap-like. Generally three to eight leaves are present, and are glabrous. Leaves tend to curl on a height of 10–15 cm, with the older outer leaves tending to take a horizontal position as depicted in FIG. 3. Flowering begins from the lowest flowers on the spike-shaped raceme, and continues upwards with flowers opening over the course of 30 to 50 days. As the flowers open, the raceme itself continues elongating stretching from an initial height of 30 cm to as long as 75 cm upon termination of flowering.

Flower raceme height can be controlled by the level of shade provided. In full sun the raceme height is generally a maximum of 50 cm. As the flowers continue opening up the raceme, the bottom one senesce. Flowers are not fragrant. Dormancy and denescence of leaves and flowers occur simultaneously upon completion of flowering. As the last flower opens and senesces, the plant begins complete dormancy. For example, bulb growth does not continue after flowering.

In a typical year, flowering begins in October and is complete by December (in the Western Cape). From the time of tissue culture, 'Namib Sun' flowers about six to eight months after emerging from the laboratory. Most other *Ornithogalum dubium* will require 18 months to flower when propagated from seed. Under the growing conditions in Groot Drakenstein, South Africa, no problems with disease have been experienced while growing 'Namib Sun'.

The flowers are shallowly cup-shaped to stellate with age. Flower color is RHS7B yellow ranging to RHS 13B, with a green heart, and fades with age. The perianth-segments are ovate and 10–20 mm long. The stamens are about half as long, with filaments having fleshy winged membranous involute expansions. The ovary is an oblong ovoid, green/brown in color. The ovules are multiseriate. The style is very short. The stigma is capitate, trisulcate, with three decurrent papillate ridges. 50 to 60 flowers are present per inflorescence.

The colors of 'Namib Sun' which follow are defined by reference to The Royal Horticultural Society (RHS) color chart. The flower stem is RHS 141B. Upper foliage is RHS 141B. Lower foliage is RHS 141B. The green color of the central part of the opened flower is RHS 141B. The bulb's scales are white RHS 155D. The bulb is covered with one or two dry scale layers that are cream to light brown (RHS 161C). The seeds are black RHS 202A, approximately 1 mm long and comma-shaped.

The preceding description describes the plant during flowering. Flowering occurs about 4–5 months after planting. Growing condition were as follow: temperature 16–28 degrees C., light level 40% shade as produced by shade cloth over a polyethylene-clad greenhouse corresponding to approximately 2,000 lux, fertilizer was applied as osmicote 3-1-5 at a rate of 5 kg/cubic meter of soil mix, and the plants were irrigated as required. The plants spread to a 20 cm diameter after 5 months during flowering in a plastic-covered tunnel.

Normally 5–6 flowers open at the same time. An individual bloom will last 7–10 days. The diameter of an individual flower is 2–3 cm.

Figure 1:
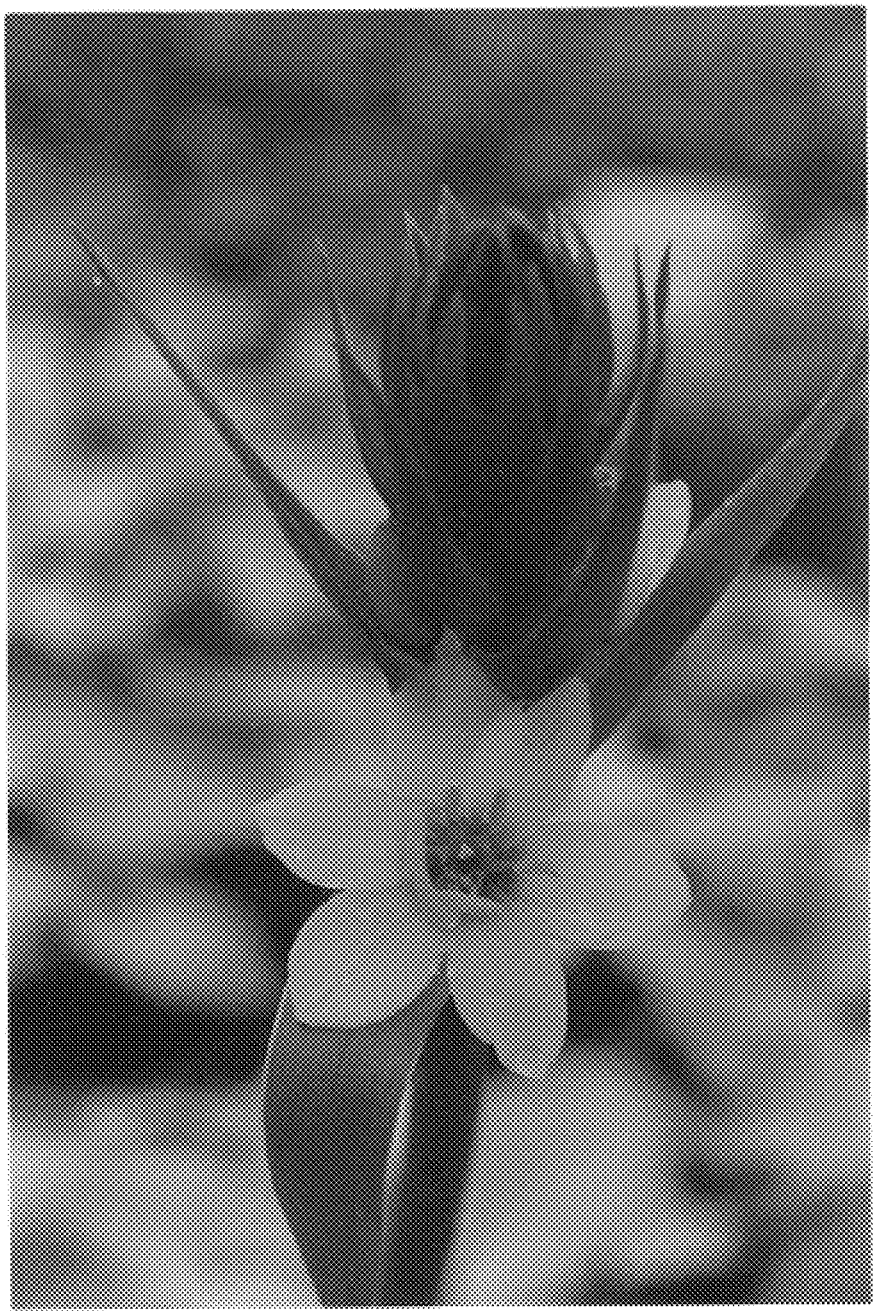
FIG. 1 is a color photograph of the upper portion of a 'Namib Sun' plant with one flower in full bloom, and two additional flowers beginning to open.
Figure 2:
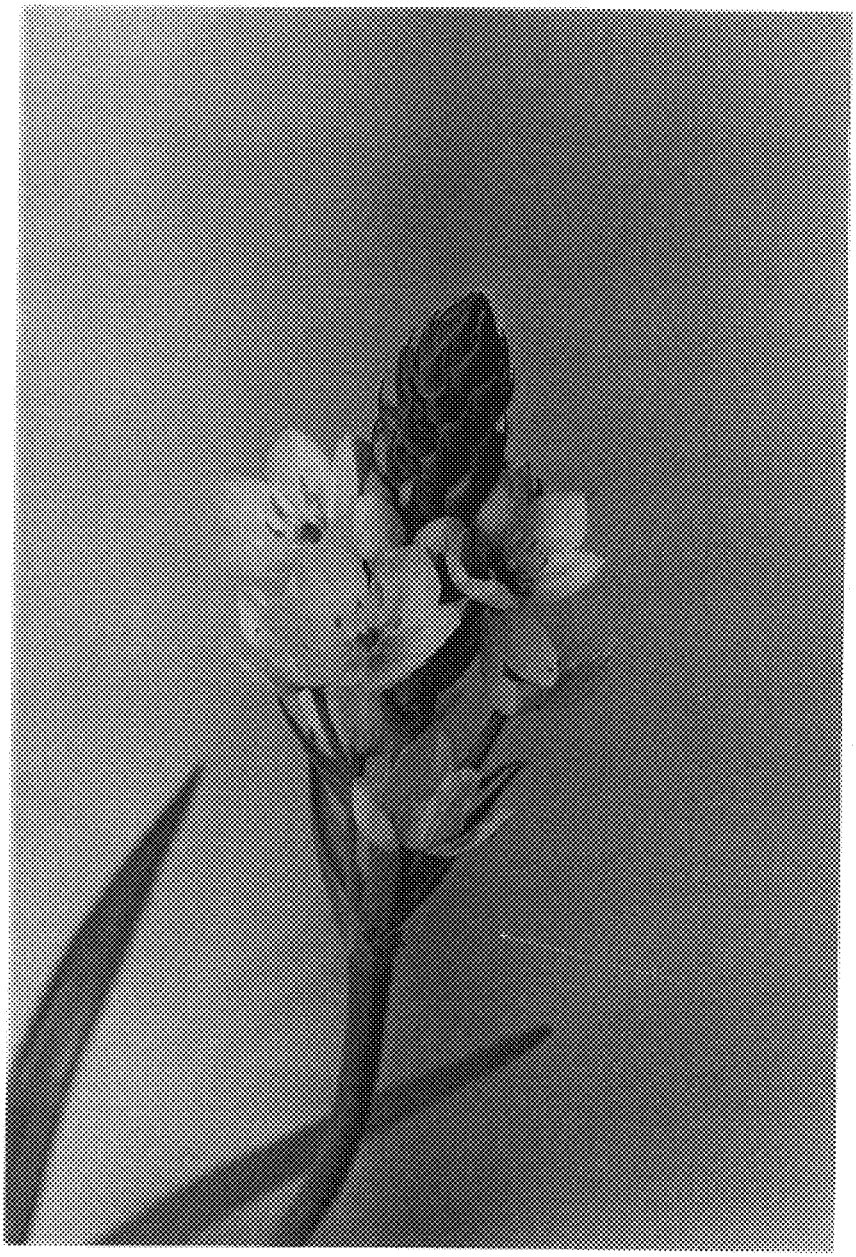
FIG. 2 is a color photograph of the upper portion of a 'Namib Sun' plant with seven flowers in full bloom, and two additional flowers beginning to open.

The flower's ovary develops into the fruit by enlarging if seeds were set. Six tepals are present, shaped as illustrated in FIG. 1. The fruit, a capsule, is oblonged, green (RHS 141B) and about 15 mm long. If no seed was set the ovary shrinks and dries together with the petals. The fruit stay on the plant until it releases the seed. Seed will only set if pollination was successful by insect or hand pollination. Seedset and fertility is expected to be low.

The leaf has a smooth margin. The tip is lance-shaped. The leaf base is white (RHS 155D) and wide as the leaf.

I claim:

1. A new and distinct cultivar of *Ornithogalum dubium* plant named 'Namib Sun', substantially as shown and described.

* * * * *

UNITED STATES PATENT AND TRADEMARK OFFICE

CERTIFICATE OF CORRECTION

PATENT NO. : PP 12,184 P2
DATED : November 6, 2001
INVENTOR(S) : Littlejohn et al.

It is certified that error appears in the above-identified patent and that said Letters Patent is hereby corrected as shown below:

Column 3,
Line 22, "No new paragraph." should be -- New paragraph at "Namib Sun…". --
Line 54, "30 - 50 days…" should be -- 30 - 60 days… --
Line 64,"...one…" should be -- ones… --

Column 4,
Line 1, "...denescence…" should be -- …senescence… --

Signed and Sealed this

Twentieth Day of August, 2002

*Attest:*

*Attesting Officer*

JAMES E. ROGAN
*Director of the United States Patent and Trademark Office*